US00PP08250P

United States Patent [19]

Trees

[11] Patent Number: Plant 8,250

[45] Date of Patent: Jun. 8, 1993

[54] POINSETTIA PLANT—BFP-437G CULTIVAR

[75] Inventor: Scott C. Trees, Arroyo Grande, Calif.

[73] Assignee: George J. Ball, Inc., West Chicago, Ill.

[21] Appl. No.: 843,932

[22] Filed: Feb. 21, 1992

[51] Int. Cl.[5] ..... A01H 5/00

[52] U.S. Cl. ..... Plt./86.4

[58] Field of Search ..... Plt./86.4

[56] References Cited

U.S. PATENT DOCUMENTS

P.P. 6,150 4/1988 Hrebeniuk ..... Plt. 86
4,724,276 2/1988 Ecke, Jr. ..... 800 1

OTHER PUBLICATIONS

"Promotion and Inhibition of Branching in Poinsettia in Grafts Between Self-Branching and Nonbranching Cultivars", D. P. Stimart, J. Amer. Soc., Hort. Sci. 108(3):419–422 (1983).

"Vegetative and Reproductive Characteristics of Poinsettia Altered by a Graft-Transmissible Agent", J. M. Dole and H. F. Wilkins, J. Amer. Hort. Soc. Sci. 116(2):307–311 (1991).

*Primary Examiner*—James R. Feyrer
*Assistant Examiner*—Erich Veitenheimer
*Attorney, Agent, or Firm*—Burns, Doane, Swecker & Mathis

[57] ABSTRACT

A new and distinct *Euphorbia pulcherrima* cultivar named BFP-437G is provided which exhibits attractive long-lasting Current Red bracts and dark green foliage. This new cultivar is the product of a phenotypical transformation following grafting (as described). A number of characteristics of the Dynasty (H518) cultivar U.S. Plant Pat. No. 6,150) are transformed upon grafting to an understock of the LADY cultivar (U.S. Plant Pat. No. 3,763) to yield a stable and distinctive new cultivar which exhibits a combination of characteristics which are incapable of prediction in advance. More specifically, the new cultivar when compared to its Dynasty (H518) parent exhibits, inter alia, more and quicker root formation, a shorter flowering response period, larger bracts particularly on developing plants, more response to growth regulators, a fuller growth habit with more extensive basal branching, and superior leaf and bract retention following harvest.

3 Drawing Sheets

SUMMARY OF THE INVENTION

The present invention concerns a new and distinct Poinsettia cultivar, botanically known as *Euphorbia pulcherrima*, and hereinafter is referred to by the cultivar name BFP-437G.

The new cultivar is the product of a phenotypical transformation which was found to be capable of induction by grafting. The utilization of grafting to bring about some types of transformation is discussed in (1) J. Amer. Soc. Hort. Sci. 108: 419–422 (1983) entitled "Promotion and Inhibition of Branching in Poinsettia in Grafts Between Self-Branching and Nonbranching Cultivars" by D. P. Stimart, (2) U.S. Pat. No. 4,724,276 to P. Ecke, Jr., and (3) J. Amer. Hort. Soc. Sci. 116(2): 307–311 (1991) entitled "Vegetative and Reproductive Characteristics of Poinsettia Altered by a Graft-Transmissible Agent" by J. M. Dole and H. F. Wilkins.

The new cultivar was created during 1990 at Santa Maria, Calif., through the selection and grafting of a specific Poinsettia scion cultivar and a specific Poinsettia rootstock cultivar which yielded a product following transformation of the scion cultivar having a novel combination of characteristics which was neither described nor even remotely suggested in the published literature. More specifically, the scion cultivar was the Dynasty (H518) cultivar (U.S. Plant Pat. No. 6,150) and the rootstock cultivar was the LADY cultivar (U.S. Plant Pat. No. 3,763). The Dynasty (H518) cultivar sometimes is known as the REGAL VELVET cultivar and such name appears in the accompanying photographs.

The initial selection following approach grafting was made during December 1990, and asexual propagation was first carried out in a controlled environment during April, 1991, through the use of vegetative cuttings at Santa Maria, Calif. A more detailed horticultural examination of selected plants was initiated at Santa Maria, Calif. during August, 1991, and has confirmed that the novel combination of characteristics of the new BFP-437G cultivar are firmly fixed and are retained in successive generations of asexual reproduction through the use of vegetative cuttings.

It surprisingly has been found that a combinatin of the characteristics of the Dynasty (H518) cultivar are modified in a stable manner to yield the new cultivar of the present invention. More specifically, the new BFP-437G cultivar when compared to its scion parent:

(a) exhibits a propensity to root substantially earlier with the formation of more fibrous roots,
(b) exhibits under natural short days a response period to initiate bract coloration of 7½ vs. 8½ weeks when grown in central California,
(c) exhibits a larger bract size particularly on developing plants,
(d) forms attractive long-lasting Current Red bracts,
(e) is more responsive to growth regulators,
(f) exhibits more extensive basal branching, and
(g) exhibits superior post-harvest qualities such as leaf and bract retention.

The BFP-437G cultivar is extremely freely branching when compared to the Dynasty (H518) cultivar and presents a fuller, more aesthetically pleasing display. The stronger branch attachment to stems translates into superior shipping characteristics with good retention of leaves and bracts. Since the time for the rooting of cuttings is one to two weeks faster than that of the Dynasty (H518) cultivar a saleable plant is produced at least one week earlier thereby increasing the output of given propagation facility with a corresponding decrease in unit cost. The new cultivar also has been found to grow and flower well under a variety of greenhouse conditons including cool and warm environments. Also, commonly six to eight breaks will occur per pinch vs. three or four at most for the parent Dynasty (H518) cultivar. Each of the sixe to eight breaks commonly will produce a flower.

The highly advantageous combination of characteristics of the new cultivar have been further confirmed during the course of trials carried out in greenhouses in Illinois, Florida, and California.

When plant material of the BFP-437G cultivar is subjected to standard random amplified polymorphic DNA marker analysis (RAPD) using polymerase chain reaction (PCR) and a known unique set of DNA primers, it is found to exhibit a distinctive fingerprint map which is on file at the Ball FloraPlant Division of George J. Ball, Inc. at Arroyo Grande, Calif.

The BFP-437G cultivar has not been observed under all possible environmental conditions to date. Accordingly, it is possible that the phenotype may vary somewhat with variations in the environment, such as temperature, light intensity and day length.

It is contemplated that the new cultivar will be marketed under the Peace Dynasty Red trademark.

BRIEF DESCRIPTION OF THE PHOTOGRAPHS

The accompanying photographs show as nearly true as it is reasonably possible to make the same in a color illustration of this character, typical specimens of the new cultivar.

FIG. 1 illustrates the parent Dynasty (H518) cultivar on the left which is identified as "Regal Velvet". The new BFP-437G cultivar is illustrated on the right and is identified as "437G". Each plant is in saleable condition and was photographed during December, 1991, while present in trials being conducted at the University of Florida, Gainesville, Fla. Cuttings were placed on OASIS-brand cubes on the same date, the rooted cuttings were transplanted on Sep. 10, 1991 to six-inch pots containing METROMIX 500-brand growth medium, the plants were pinched on Oct. 2, 1991, and short days commenced on Oct. 16, 1991. The greenhouse was maintained at an average daytime temperature of 83° F. and an average nighttime temperature of 64° F. Cycocel (1500 ppm) and B-9 (2500 ppm) growth regulators were twice applied to the plants which accounts for the more compact growth habit which is considerably more pronounced on the BFG-437G cultivar. The Current Red bract coloration of the new cultivar is more accurately depicted here than in FIG. 2.

FIG. 2 illustrates the parent Dynasty (H518) cultivar on the left which is identified as "Regal Velvet". The new VFP-437G cultivar is illustrated on the right and is identified as "437G". The plants are of the same age and were photographed during January, 1992 while present in trials conducted at Santa Maria, Calif. Cuttings were placed on OASIS-brand cubes on Aug. 30, 1991, the rooted cuttings were transplanted on Sep. 23, 1991 to six-inch pots containing Sunshine No. 2 growth medium, the plants were pinched on Oct. 6, 1991, and the short days commenced on Nov. 18, 1991. The greenhouse was maintained at an average daytime temperature of 70° to 75° F. and an average nighttime temperature of 55° to 60° F. No growth regulator was utilized. The disparity in growth habit, earliness, and bract and leaf size is apparent. The bract coloration in this photograph is considered not to be as accurate as that shown in FIG. 1.

FIG. 3 illustrates on Sep. 23, 1991 a cutting of the DYNASTY (H518) cultivar on the right which is labeled "Regal Velvet", and a cutting of the BFP-437G cultivar on the left which is identified as "437-G". These cuttings are each of the same age and were observed during trials conducted at Santa Maria, Calif. Initially each cutting was placed in an OASIS-brand cube and mist treatment was commenced on Aug. 30, 1991. It will be noted that the BFP-437G cultivar has formed numerous fibrous roots and lateral branching has already begun at this stage of the plant's life. An insignificant amount of rooting and no lateral branching is apparent on the Dynasty (H518) cultivar.

DETAILED DESCRIPTION

Figure 1:
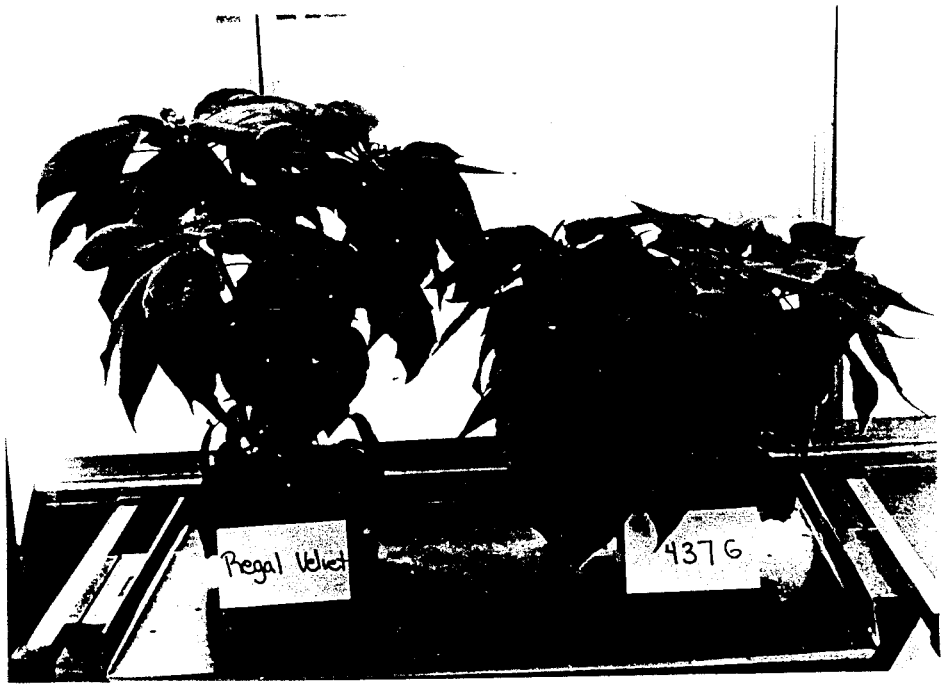
Figure 2:
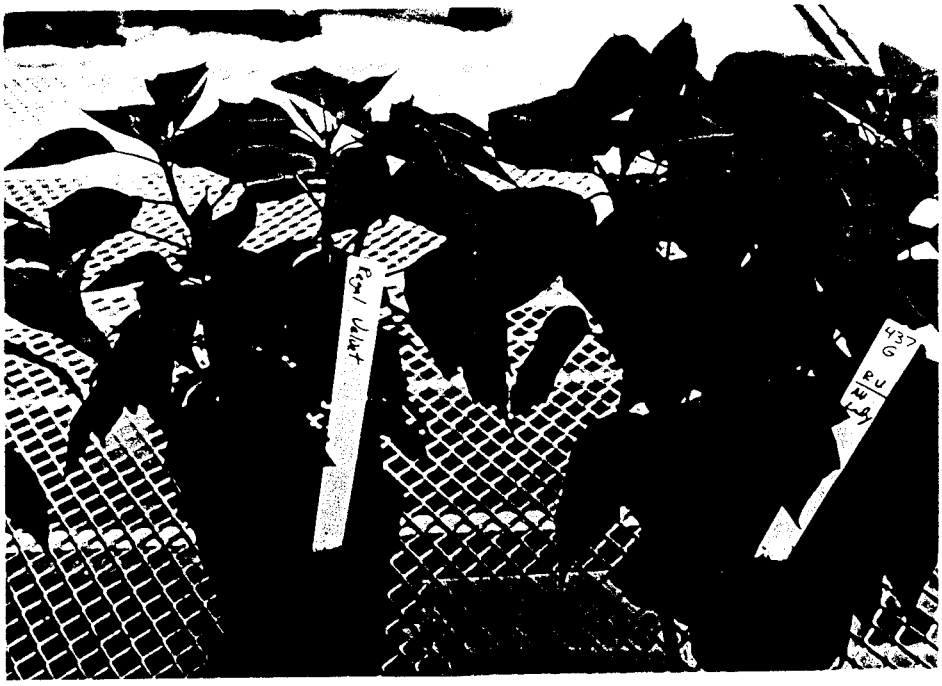
Figure 3:
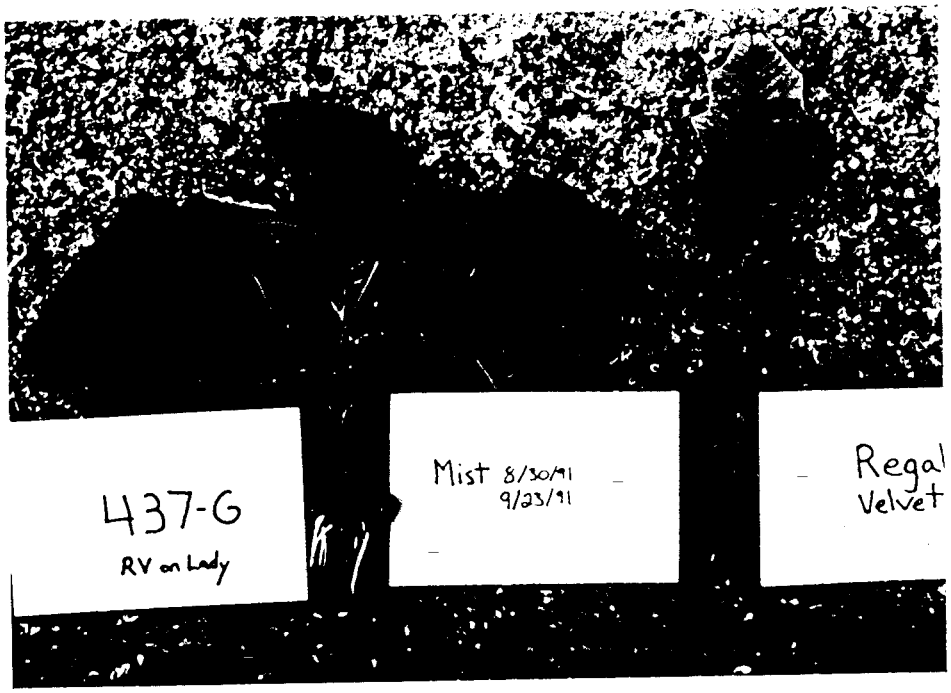

The chart used in the identification of colors described herein is The R.H.S. Colour Chart of the Royal Horticultural Society, London, England. Color terminology in common terms precedes the reference to The R.H.S. Colour Chart information. The color values were determined on Jan. 27, 1992 at 11:00 a.m. to 12:00 noon using a light intensity of 5,000 footcandles at Santa Maria, Calif. The plants described were grown under standard greenhouse conditions.

Classification:

*Botanical.*—*Euphorbia pulcherrima.*

*Commercial.*—Poinsettia.

Parentage:

*Scion parent.*—Dynasty (H518) cultivar (U.S. Plant Pat. No. 6,150).

*Rootstock parent.*—Lady cultivar (U.S. Plant Pat. No. 3,763).

Plant:

*Form.*—Vase-shaped.

*Growth habit.*—Upright, compact, and freely branching following pinching.

*Rooting.*—Well-rooted following approximately 14 to 21 days in Oasis-brand cubes while the Dynasty (H518) cultivar requires approximately 7 to 14 days longer to root under the same conditons.

*Blooming season.*—Under natural short days at Santa Maria, Calif., from approximately December 1st to approximately January 15th.

*Blooming habit.*—Large oval-shaped bracts turning color in response to short days.

*Foliage size.*—Approximately 5½ to 9½ cm. in width and approximately 9½ to 13½ cm. in length.

*Foliage quantity.*—Approximately 7 to 10 leaves per flowering stem depending upon the culture experienced.

*Foliage color.*—New foliage: Green Group 135A on the upper side and Green Group 137B on the underside. Old foliage: Green Group 136A on the upper side, Green Group 139A on the underside, and Red Group 46A on the leaf petiole.

*Foliage configuration.*—The leaves are basically ovate, possess margins ranging from repand to slightly crenate, possess a variable leaf edge margin and a pointed tip.

*Foliage texture.*—Dull and display prominent veins on the underside which approximate Red Group 47A.

*Disease resistance.*—Resistant to Botrytis, and slightly susceptible to powdery mildew under conditions conductive to the disease.

Flowers:

*Borne.*—In a compound corymb.

*Reproductive organs.*—Approximately 10 to 12 per stem, held tightly together, most with one nectary, some with two nectaries, commonly resist premature drop.

*Bract color.*—Current Red Group 46A.

*Bract size.*—Approximately 2½ to 10½ cm. in width and approximately 4½ to 15½ cm. in length on a pinched plant grown in a greenhouse at an average daytime temperature of 70° to 75° F. and an average nighttime temperature of 65° F. while exposed to natural day length.

I claim:

1. A new and distinct cultivar of Poinsettia plant resulting from a phenotypical transformation of the Dynasty (H518) scion cultivar (U.S. Plant Pat. No. 6,150) when grafted on a rootstock of the LADY cultivar (U.S. Plant Pat. No. 3,763), substantially as herein illustrated and described, wherein the following characteristics are present when compared to the Dynasty (H518) cultivar:

(a) exhibits a propensity to root substantially earlier with the formation of more fibrous roots,
(b) exhibits under natural short days a response period to initiate bract coloration of 7½ vs. 8½ weeks when grown in central California,
(c) exhibits a larger bract size particularly on developing plants,
(d) forms attractive long-lasting Current Red bracts,
(e) is more responsive to growth regulators,
(f) exhibits more extensive basal branching, and
(g) exhibits superior post-harvest qualities such as leaf and bract retention.

* * * * *